United States Patent
Amanullah et al.

(10) Patent No.: US 10,508,978 B2
(45) Date of Patent: Dec. 17, 2019

(54) STRAIN ENERGY-BASED METHOD AND APPARATUS TO DETERMINE THE COEFFICIENT OF RESILIENCE OF LOST CIRCULATION MATERIALS

(71) Applicant: Saudi Arabian Oil Company, Dhahran (SA)

(72) Inventors: Md Amanullah, Dhahran (SA); Mohammed K. Arfaj, Dhahran (SA); Turki Alsubaie, Alkhobar (SA)

(73) Assignee: Saudi Arabian Oil Company, Dhahran (SA)

(*) Notice: Subject to any disclaimer, the term of this patent is extended or adjusted under 35 U.S.C. 154(b) by 236 days.

(21) Appl. No.: 15/802,870

(22) Filed: Nov. 3, 2017

(65) Prior Publication Data
US 2019/0137371 A1    May 9, 2019

(51) Int. Cl.
| | |
|---|---|
| *G01N 3/08* | (2006.01) |
| *G01N 11/00* | (2006.01) |
| *G01B 21/16* | (2006.01) |
| *E21B 43/12* | (2006.01) |

(52) U.S. Cl.
CPC .............. *G01N 3/08* (2013.01); *E21B 43/12* (2013.01); *G01B 21/16* (2013.01); *G01N 11/00* (2013.01); *G01N 2203/0092* (2013.01)

(58) Field of Classification Search
CPC ........... G01N 3/08; G01N 11/00; G01B 21/16
See application file for complete search history.

(56) References Cited

U.S. PATENT DOCUMENTS

| | | |
|---|---|---|
| 3,448,800 A | 6/1969 | Parker et al. |
| 7,219,732 B2 | 5/2007 | Reddy |
| 7,776,797 B2 | 8/2010 | Allin et al. |
| 7,799,743 B2 | 9/2010 | Way et al. |
| 8,132,623 B2 | 3/2012 | Allin et al. |
| 8,151,633 B2 | 4/2012 | Jamison et al. |
| 8,464,592 B2 | 6/2013 | Hirtt et al. |
| 8,972,235 B2 | 3/2015 | Murphy et al. |

(Continued)

FOREIGN PATENT DOCUMENTS

| | | |
|---|---|---|
| CN | 101122597 A | 2/2008 |
| CN | 101482474 A | 7/2009 |

(Continued)

OTHER PUBLICATIONS

International Search Report and Written Opinion for International PCT application PCT/US2018/058608 dated Mar. 8, 2019; pp. 1-15.

(Continued)

*Primary Examiner* — Jamel E Williams
(74) *Attorney, Agent, or Firm* — Bracewell LLP; Constance G. Rhebergen; Brian H. Tompkins

(57) ABSTRACT

A portable resilience testing apparatus for lost circulation materials (LCMs) is provided. The portable resilience testing apparatus includes a test cell and a probe that moves and applies a force to a sample of LCM contained in the test cell. The portable resilience testing apparatus may be used to perform a compression cycle and decompression cycle on the LCM sample. A coefficient of resilience of the LCM sample is determined from the desorbed strain energy released during the decompression and the absorbed strain energy stored during the compression cycle. A method of determining the coefficient of resilience is also provided.

20 Claims, 5 Drawing Sheets

(56) References Cited

U.S. PATENT DOCUMENTS

| | | | |
|---|---|---|---|
| 9,714,565 | B2 | 7/2017 | Blue et al. |
| 2009/0306898 | A1 | 12/2009 | Anschutz et al. |
| 2012/0152000 | A1 | 6/2012 | Jamison et al. |

FOREIGN PATENT DOCUMENTS

| | | |
|---|---|---|
| CN | 104897464 A | 9/2015 |
| JP | 05072086 B2 | 3/1993 |
| SU | 1357495 | 12/1987 |

OTHER PUBLICATIONS

Yan et al., "Compressional resilience of the kapok fibrous assembly", Textile Research Journal, 2014, vol. 84, No. 13; pp. 1441-1450.

Yaoet al., "Test Method for Compression Resilience Evaluation of Textiles", TELKOMNIKA, 2013, vol. 11, No. 2, Feb. 2013; pp. 674-680.

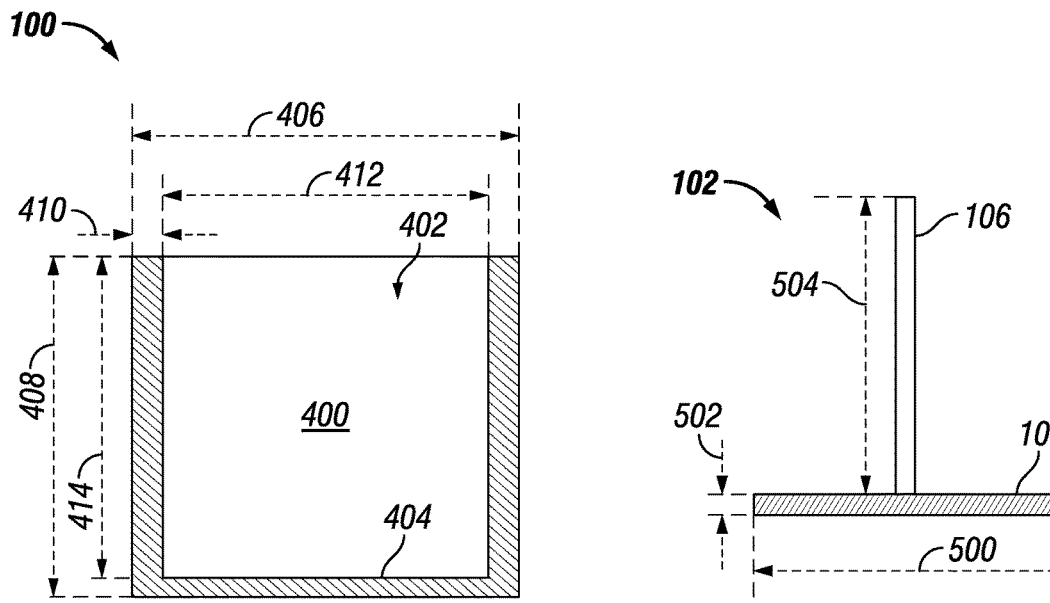
FIG. 4
FIG. 5
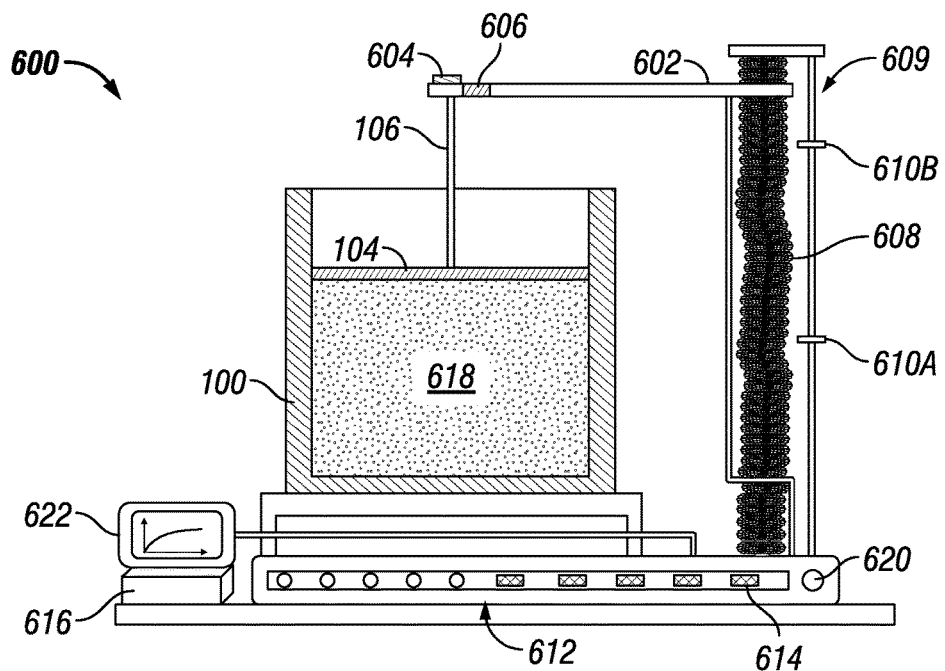
FIG. 6

STRAIN ENERGY-BASED METHOD AND APPARATUS TO DETERMINE THE COEFFICIENT OF RESILIENCE OF LOST CIRCULATION MATERIALS

BACKGROUND

Field of the Disclosure

The present disclosure generally relates to the testing and evaluation of lost circulation materials (LCMs) used to control lost circulation in a wellbore during drilling with a drilling fluid. More specifically, embodiments of the disclosure relate to the determining the resilient behavior or lost circulation materials (LCMs).

Description of the Related Art

Lost circulation is one of the frequent challenges encountered during drilling operations. Lost circulation can be encountered during any stage of operations and occurs when drilling fluid (or drilling mud) pumped into a well returns partially or does not return to the surface. While some fluid loss is expected, excessive fluid loss is not desirable from a safety, an economical, or an environmental point of view. Lost circulation is associated with problems with well control, borehole instability, pipe sticking, unsuccessful production tests, poor hydrocarbon production after well completion, and formation damage due to plugging of pores and pore throats by mud particles. Lost circulation problems may also contribute to non-productive time (NPT) for a drilling operation. In extreme cases, lost circulation problems may force abandonment of a well.

Lost circulation can occur in various formations, such as naturally fractured formations, cavernous formations, and high permeable formations. Lost circulation can be categorized by the amount of fluid or mud lost, such as seepage type, moderate type, severe type, and total loss. The extent of the fluid loss and the ability to control the lost circulation with an LCM depends on the type of formation in which the lost circulation occurs. Some formations, such as vugular and cavernous formations, may require particular types of LCMs to prevent or mitigate through the vugs and fractures in such formations.

SUMMARY

Lost circulation materials (LCMs) are used to mitigate the lost circulation by blocking the path of the drilling fluid (such as drilling mud) into the formation. The type of LCM used in a lost circulation situation depends on the extent of lost circulation and the type of formation. Different types of LCMs such as granular, fibrous and flaky materials are frequently used either alone or in combination to control loss of circulation. The costs incurred in lost circulation situations may be due to lost time, losses of drilling fluids, and losses of production. Existing LCMs may perform poorly in mitigation and prevention of moderate and seepage type lost circulation, and may not be suitable for controlling severe loss of circulation.

Some LCMs may be used to create resilient seals or plugs in a loss zone. Such LCMs may include particles intended to enter into loss zone gaps, cracks, fractures and vugs, and then expand after the cessation of overbalance pressure to create seals or plugs in the loss zone gaps, cracks, fractures and vugs to control loss of circulation. However, there is no standardized test or other industry method for evaluating the resilient characteristics of such LCM compositions.

In one embodiment, an apparatus for determining the coefficient of resilience of a lost circulation material (LCM) is provided. The apparatus includes a test cell having an interior chamber configured to contain a sample of the LCM, such that the test cell has an open end and closed end defining the interior chamber. The apparatus also includes a probe configured to insert into the open end of the test cell and having a disc-shaped probe foot and a probe leg. The apparatus further includes an arm coupled to the probe and configured to apply a load to the probe such that a force is applied to the LCM sample via movement of the probe over a first displacement during a compression cycle and further configured to release the load applied to the probe such that the force is removed via movement of the probe over a second displacement during a decompression cycle. Additionally, the apparatus includes a processor and a non-transitory computer-readable memory accessible by the processor and having executable code stored thereon. The executable code includes a set of instructions that causes the processor to perform operations that include determining a strain energy absorbed by the LCM sample during the compression cycle using the first displacement, determining a strain energy released by the LCM sample during a decompression cycle using the second displacement, and determining a coefficient of resilience by dividing the released strain energy by the absorbed strain energy. In some embodiments, the operations include providing a plot of force versus distance based on the force applied to the LCM sample and the distance between the first position and the second position on a display accessible by the processor. In some embodiments, the apparatus includes a base, such that the test cell is coupled to the base. In some embodiments, the arm is coupled to the base via a movement mechanism. In some embodiments, the base includes a port, such that the port is configured to connect the base to the processor via a wired connection. In some embodiments the probe arm and probe leg are aluminum. In some embodiments, the movement of the probe over the first displacement occurs between a first position and a second position, and the movement of the probe over the second displacement occurs between the second position and the third position. In some embodiments, the first position and the third position are the same. In some embodiments, the arm is further configured to maintain the probe in the second position for a time period before movement of the probe to the third position.

In another embodiment, a method for determining the coefficient of resilience of a lost circulation material (LCM) is provided. The method includes applying a force to LCM a sample of the LCM contained in a test cell via movement of a probe inserted into an open end of a test cell from a first position to a second position during a compression cycle, such that the first position and second position define a first displacement. The method further includes determining a strain energy absorbed by the LCM sample using the first displacement and releasing the force applied to the LCM sample via displacement of the probe from the second position to a third position during a decompression cycle, such that the second position and third position define a second displacement. The method also includes defining a strain energy released using the second displacement and determining a coefficient of resilience by dividing the released strain energy by the absorbed strain energy. In some embodiments, the force is at least 3 grams-force (gf). In some embodiments, the movement of the probe occurs over a displacement rate. In some embodiments, the displacement rate is at least 1 millimeter/second (mm/sec). In some embodiments, the method includes maintaining the probe in the second position for a time period. In some embodiments, the time period is at least one minute. In some embodiments, the first position and the third position are the same.

In another embodiment, an apparatus for determining the coefficient of resilience of a lost circulation material (LCM). The apparatus includes a base having a control circuit and a power source, a test cell coupled to the base and having an interior chamber configured to contain a sample of the LCM, the test cell having an open end and closed end defining the interior chamber, a probe configured to move within the interior chamber of the test cell, a connecting rod coupled to the base, and an arm coupled to the probe. The arm is configured to apply a load to the probe in response such that a force is applied to the LCM sample via movement of the probe over from a first position to a second position during a compression cycle and is further configured to release the load applied to the probe such that the force is removed via movement of the probe from the second position to a third position during a decompression cycle, such that the first position and the second position define a first displacement of the probe and the second position and the third position define a second displacement of the probe. In some embodiments, the arm is further configured to maintain the probe in the second position for a time period before movement of the probe to the third position. In some embodiments, the first position and the third position are the same. In some embodiments, the apparatus includes a first position limiter coupled to the connecting rod and a second position limiter coupled to the connecting rod, such that the first position limiter is configured to define the second position of the probe and the second position limiter is configured to engage the arm to define the third position of the probe.

BRIEF DESCRIPTION OF THE DRAWINGS

FIG. 4 is a cross-sectional view of a test cell of an apparatus for determining the coefficient of resilience of an LCM in accordance with an embodiment of the disclosure;

FIG. 5 is a cross-sectional view of a probe of an apparatus for determining the coefficient of resilience of an LCM in accordance with an embodiment of the disclosure;

FIG. 6 is a schematic diagram of portable apparatus for determining the coefficient of resilience of an LCM in accordance with an embodiment of the disclosure;

DETAILED DESCRIPTION

Figure 1:
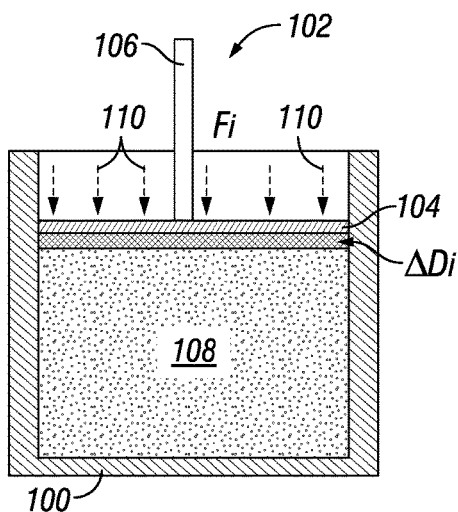
FIG. 1 is a cross-sectional view of a test cell and probe of an apparatus for determining the coefficient of resilience of an LCM in accordance with an embodiment of the disclosure.

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure include the determination of a coefficient of resilience (COR) of a lost circulation material (LCM). The coefficient of resilience is determined based on strain energy absorption while compressing an LCM sample and strain energy desorption while decompressing an LCM sample. Based on the strain energy absorbed during a compression cycle (also referred to as a "loading cycle") and strain energy released during a decompression cycle (also referred to as an "unloading cycle"), the coefficient of resilience may be determined as the ratio of strain energy desorbed to the strain energy absorbed. The coefficient of resilience may provide a quantitative assessment of the resilient characteristics of an LCM, Various LCMs may be tested and evaluated based on the coefficient of resilience to identify resilient LCMs suitable for forming seals and plugs in loss zone gaps, cracks, fractures and vugs after the cessation of overbalance pressure to control loss of circulation.

Embodiments of the disclosure further include a portable resilience testing apparatus for determining the coefficient of resilience of a lost circulation material (LCM). The portable resilience testing apparatus includes a cylindrical test cell with an open end and a closed end and a probe that applies a load on the sample top placed in the test cell. The probe includes a flat foot disc piston made of aluminum that is attached to cylindrical leg that connects to a load cell of a load cell carrier arm. The portable resilience testing apparatus further includes a movement mechanism attached to the load cell carrier arm that applies a load to the sample in the test cell. The portable resilience testing apparatus includes a connecting rod coupled to position limiters to define the movement of the aluminum probe. The portable resilience testing apparatus may include or be coupled to a base having control circuitry for controlling a resilience test. The portable resilience testing apparatus may also be coupled to a computer for display of resilience testing data and determination of a coefficient of resilience.

Embodiments of the disclosure further include a process for determining the coefficient of resilience using the apparatus described in the disclosure includes positioning a sample into the test cell, positioning the aluminum probe and setting testing parameters (such as a trigger force), and performing a compression cycle and recording the total energy absorbed at the end of the compression cycle. After performing the compression cycle, the probe may be held in its loading cycle position for a loading time period. The process further includes performing a decompression cycle by withdrawing the probe at a displacement rate and then recording the total energy released after withdrawing the probe. The coefficient of resilience may be determined by dividing the desorbed strain energy released during the decompression cycle by the absorbed strain energy stored by the sample during the compression cycle.

FIG. 1 depicts a test cell 100 and probe 102 of an apparatus for determining the coefficient of resilience of an LCM in accordance with an embodiment of the disclosure. The test cell 100 may be generally cylindrical shaped and is configured to receive a probe foot 104 of the probe 102. The probe 102 includes the probe foot 104 coupled to a probe leg 106 that is coupled to a movement mechanism. In some embodiments, the probe foot 104 and the probe leg 106 may be aluminum or an aluminum alloy.

The operation of the test cell 100 and probe 102 enables the determination of a coefficient of resilience of a sample. As shown in FIG. 1, a sample 108 of an LCM may be positioned in an interior chamber of the test cell 102. A force Fi may be applied to a surface of the LCM sample 108 via the probe 102, as shown by arrows 110 in FIG. 1. The force Fi is sufficient to move the probe 102 by a displacement ΔDi in the direction of the force Fi. The force Fi may be increased by an amount ΔFi for a displacement ΔDi. If ΔFi approaches 0, the incremental work ΔW done by the force Fi from a position of zero to a displacement $\Delta D_i$ is approximately $F_i \Delta D_i$. Thus, the work performed by the force Fi for an elemental displacement $\Delta D_i$ may be expressed by Equation 1:

$$\Delta W = \int_0^{\Delta Di} Fi(Di) dDi \quad (1)$$

Figure 2:
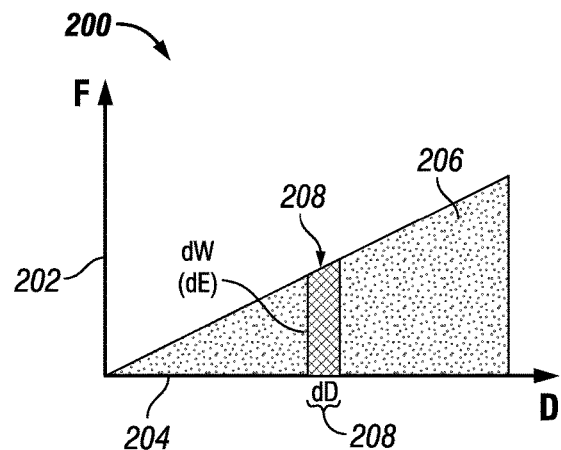
FIG. 2 is a plot of force vs. distance graphically illustrating the determination of the incremental work ΔW done by the force Fi from a position of zero to a displacement ΔD$_i$ shown in FIG. 2 and in accordance with an embodiment of the disclosure.

FIG. 2 is a plot 200 of force vs. distance graphically illustrating the determination of the incremental work done by a force from a position of zero to a displacement. As shown FIG. 2, the y-axis 202 depicts force and the x-axis 204 depicts distance. The line 206 in the plot 200 depicts an example force-displacement curve. The displacement 208 (dD) corresponding to a mean force 210 are also shown in FIG. 2. The area 210 under the force-displacement curve defined by the displacement 206 (dD) and mean force 208 corresponds to the incremental work (dW) performed by a force for a displacement 208.

If the LCM sample is perfectly elastic and resilient, then Fi(Di)=kiDi, where ki is the spring constant. Thus, the work of the force increasing from zero to Fi to compress the LCM sample from 0 to a distance Di may be expressed according to Equation 2:

$$W = \int_0^{Di} FidDi = \int_0^{Di} kiDidDi = \frac{1}{2} kiDi^2 = \frac{1}{2} 1/kiFi^2 = \frac{1}{2} FiDi \quad (2)$$

Based on Equation 2, the work performed by the compressive force Fc to compress the LCM sample to a distance of Dd is equal to the elastic energy Ea absorbed by the sample during the compression cycle of a resilience test and may be expressed by Equation 3:

$$Ea = \frac{1}{2}(Fc \times Dd) \quad (3)$$

Figure 3:
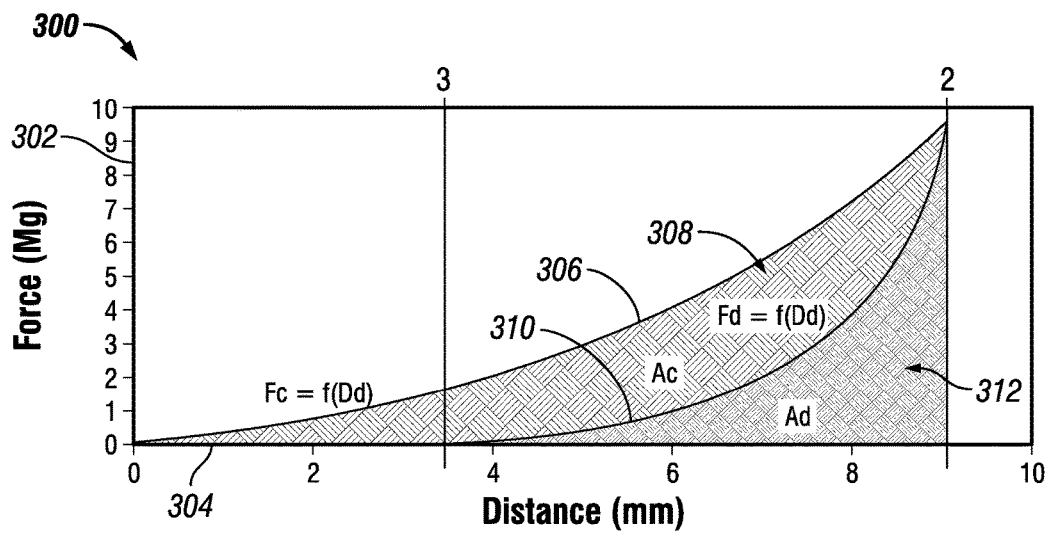
FIG. 3 is a force vs. distance graphically illustrating the determination of the elastic energy generated by a compressive force and absorbed by an LCM sample in accordance with an embodiment of the disclosure.

Graphically, the elastic energy represents the area below the load-displacement curve generated by the compressive force Fc due the downward displacement of the LCM sample to a distance Dd. For example, FIG. 3 depicts a plot 300 of force vs. distance graphically illustrating the determination of the elastic energy generated by a compressive force and absorbed by an LCM sample. As shown FIG. 3, the y-axis 302 depicts force and the x-axis 304 depicts distance. The line 306 in the plot 300 depicts an example force-displacement curve generated during a compression cycle (that is Fc=f(Dc)). The area Ac (indicated by reference number 308) below the curve Fc=f(Dd) represents the amount of energy absorbed during the compression cycle of the resilience test.

The work performed by the unloading force during the decompression cycle of the test is equal to the elastic energy Ed desorbed by the LCM sample during the upward displacement of the LCM sample to a distance Du and may be expressed by Equation 4:

$$Ed = \frac{1}{2}(Fd \times Du) \quad (3)$$

Graphically, the elastic energy Ed represents the area below the load-displacement curve generated by the decompression force Fd due to the upward displacement of the LCM sample to a distance Du. As shown in FIG. 3, the line 310 in the plot 300 depicts an example force-displacement curve generated during a decompression cycle (that is, the curve representing the relationship Fd=f(Du)). The area Ad (indicated by reference number 312) below the curve Fd=f(Du) represents the amount of energy desorbed during the decompression cycle of the test.

The coefficient of resilience (COR) for the LCM sample may thus be determined from the ratio of the amount of energy desorbed during the decompression cycle to the amount of energy absorbed during the compression cycle, as shown in Equation 5:

$$COR = Ad/Ac \quad (5)$$

FIGS. 4 and 5 depict further details of the test cell and probe in accordance with an embodiment of the disclosure. Accordingly, FIG. 4 depicts a cross-sectional side view of the test cell 100 in accordance with such embodiments. In some embodiments, the test cell may be generally cylindrical shaped and define an interior chamber 400 having an open end 402 and a closed end 404. As mentioned above, the open end 402 may be configured to receive the probe 102. The test cell 100 may have an outer diameter 406, a height 408, and a wall thickness 410. In some embodiments, the outer diameter 406 may be 60 mm, the height 408 may be 116 mm, and the wall thickness 410 may be 12 mm. The test cell 102 may define the interior chamber 400 having an inner diameter 412 and a height 414. In some embodiments, the inner diameter 412 may be 48 mm and the height 414 may be 104 mm. As described herein, the interior chamber is configured to receive a sample of an LCM for testing in accordance with the techniques described in the disclosure.

FIG. 5 depicts a side view of the probe 102 having the probe foot 104 coupled to the probe leg 106 in accordance with an embodiment of the disclosure. The probe foot 104 may be generally disc-shaped and may have a diameter 500 and a foot thickness 502. The diameter may be selected to ensure that the probe foot 106 is received in the interior chamber 400. In some embodiments, the diameter 500 may be about 47.5 mm and the foot thickness 502 may be 5 mm. The probe leg 106 may have a leg length 504 to enable movement of the probe 102 into the interior chamber 400 sufficient to compress an LCM sample for testing. In some embodiments, both the probe foot 104 and the probe leg 106 may be aluminum or an aluminum alloy. In some embodiments, the probe foot 104 and the probe 106 may form a single component or, in some embodiments, the probe leg 106 may be removable from the probe foot 104.

Embodiments of the disclosure further include a portable apparatus for determining the coefficient of resilience. The apparatus may be portable such that the apparatus may be transported to a well site and used to determine the coefficient of resilience of an LCM at the well site. In this manner, the suitable of LCMs available at a well site for use in lost circulation zones having specific characteristics may be determined without transporting the LCM to a testing location (for example, a laboratory) remote from the well site.

FIG. 6 depicts a portable resilience testing apparatus 600 for determining the coefficient of resilience of an LCM in accordance with an embodiment of the disclosure. The portable resilience testing apparatus 600 may include the test cell 100 and the probe 102 having the probe foot 104 and the probe leg 106 discussed above. The apparatus further includes a load cell carrier arm 602 coupled to the probe leg 106, a calibration platform 604, a load cell 606, a movement mechanism 608 coupled to the carrier arm 602, a connecting rod 609, and position limiters 610 disposed on the connecting rod 609. In some embodiments, the portable apparatus 600 may include or be coupled to a base 612 having a control panel 614. In some embodiments, the portable apparatus 600 may include or be coupled to a computer 616.

As discussed above, the test cell 100 may receive an LCM sample 618 for testing using the portable apparatus 600. FIG. 6 depicts the test cell 100 and probe 102 in cross-section illustrating the LCM sample 618 positioned in the test cell 100.

The load cell carrier arm 602 may translate up and down via the movement mechanism 608 when the portable resilience testing apparatus 600 is powered, such that the load cell 606 provides for application of a load to the LCM sample 618 via movement of the probe 102. For example, the probe foot 104 may compress the LCM sample 618 via a force applied to the top surface of the LCM sample 618. The load cell carrier arm 606 may also provide for removal of a load from the LCM sample 618 to enable decompression of the LCM sample 618 such that the probe foot 104 moves to a second position. In this manner, the load cell carrier arm 602 and load cell 606 may provide for a compression cycle of a resilience test and decompression cycle of a resilience test to enable determination of a coefficient of resilience of the LCM sample 618 using the determination described above in paragraphs 26-30 and Equations 3-5. In some embodiments, the movement mechanism 608 may be a hydraulic mechanism. In other embodiments, the movement mechanism 608 may be a rack and pinion mechanism.

The position limiters 610 are coupled to the connecting rod 609 and may define the movement of the load cell carrier arm 602 during the compression cycle and decompression cycle of the resilience test. The lower position limiter 610A may define the maximum downward displacement of the load cell carrier arm 606 during a compression cycle. When the load cell carrier arm 606 encounters the lower position limiter 610A, movement of the load cell carrier arm 606 may automatically stop and the load cell carrier arm 606 may remain in the compression position for a time period. The upper position limiter 610B may define the maximum upward displacement of the load cell carrier arm 606 during a decompression cycle. When the load cell carrier arm 606 encounters the upper position limiter 610B, movement of the load cell carrier arm 606 may automatically stop.

The calibration platform 604 enables calibration of the load cell 606 and the action of the load cell carrier arm 602. For example, the load cell may be calibrated by placing known weights on the calibration platform and recording the corresponding weight displaced by load cell 606 (for example, by viewing the displaced weight via the computer 616).

The base 612 may be of sufficient weight to prevent movement of the components of the portable resilience testing apparatus 600 during performance of resilience test. In some embodiments, the base 612 may form a housing to enclose electronic components that control and monitor operation of the portable resilience testing apparatus 600. In some embodiments, the base 612 may also include power components that enable powering of the portable resilience testing apparatus 600. In some embodiments, the power components may include a battery. In some embodiments, the power components may include components for receiving and converting power from an AC power source (for example, AC mains) to operate the portable resilience testing apparatus 600, charge a battery, or a combination thereof. In some embodiments, the exterior of the base 612 may include the control panel 614. The control panel 614 may include one or more hardware elements (for example, buttons, switches, and the like) that control operation of the resilience testing apparatus 600. In some embodiments, for example, the control panel 614 may include an Emergency Stop button 620 that, when pressed, immediately stops operation of the apparatus 614. In some embodiments, the control panel may include other elements, such as a Start button, a power button or switch, and so on.

In some embodiments, the portable resilience testing apparatus 600 may include or be coupled to a computer 616. The computer 616 may be coupled to or include a display 622. The computer 616 may receive and store the data associated with a resilience test in a non-transitory computer-readable memory. In other embodiments, the computer 616, the display 622, or both may be integrated in the base 612 of the portable resilience testing apparatus 600.

Figure 7:
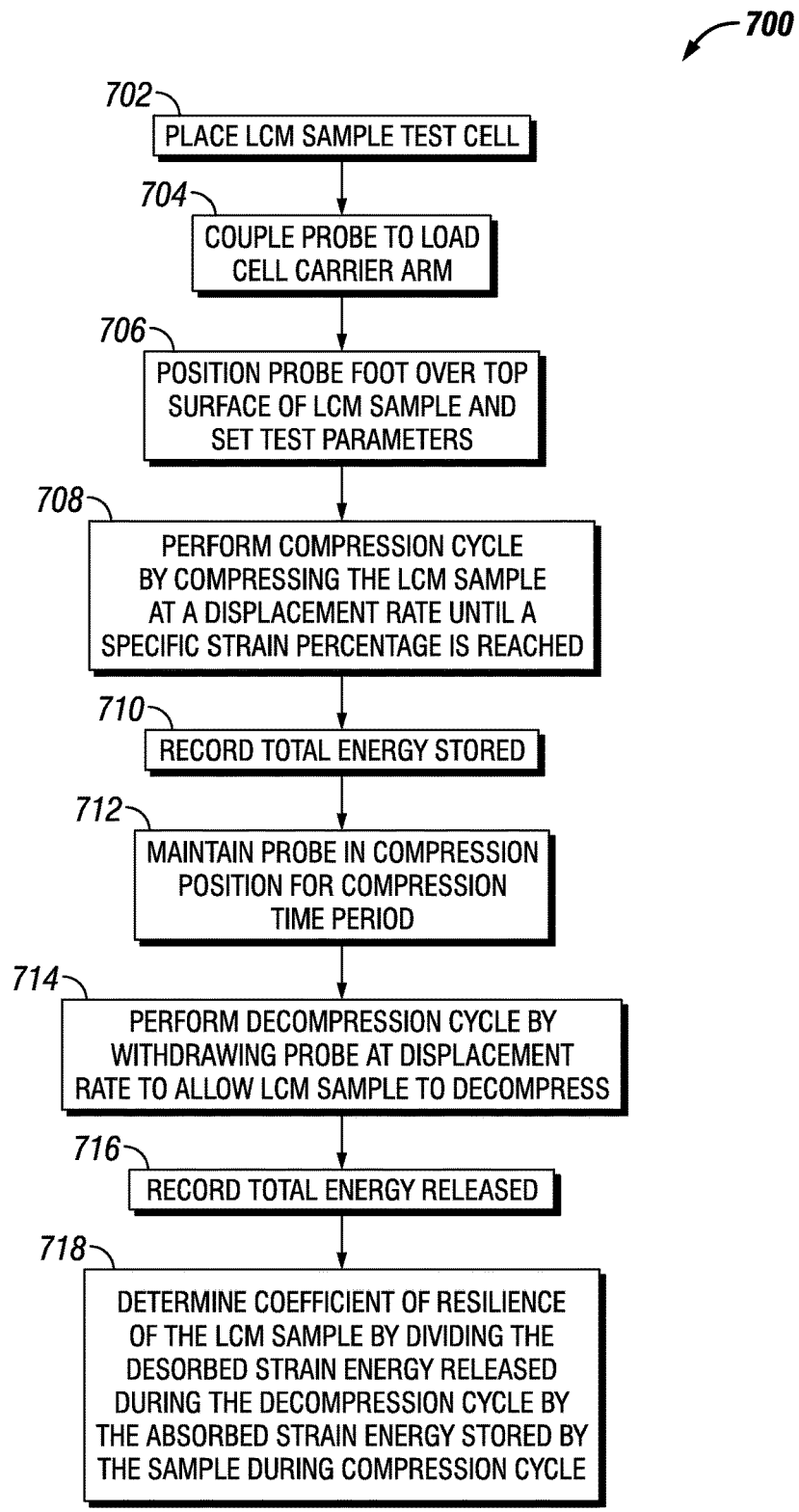
FIG. 7 is a block diagram of a process for determining the coefficient of resilience of an LCM sample using a portable resilience testing apparatus in accordance with an embodiment of the disclosure.

FIG. 7 depicts a process 700 for determining the coefficient of resilience of an LCM sample using the resilience testing apparatus described herein in accordance with an embodiment of the disclosure. As will be appreciated, the process 700 may be performed at a well site using the portable resilience testing apparatus 600, thus eliminating the requirement to send a sample of a LCM to a remote location for testing and evaluation. The portable resilience apparatus 600 may thus reduce the costs and time associated with evaluation of LCMs for use at a well site. Initially, as shown in FIG. 7, LCM sample may be placed into the test cell such that the top of the LCM sample is at a distance below the open end of the test cell and the top is level (block 702). In some embodiments, the LCM sample may be placed in the test cell such that the LCM sample is 2 centimeters (cm) below the top of the test cell.

The probe with the probe foot and probe leg may then be coupled to the load cell carrier arm (704). The probe foot may be positioned over the top surface of the LCM sample and test parameters may be set (block 706). In some embodiments, for example, a trigger force to be applied to the LCM sample may be set. In some embodiments, the trigger force may be at least about 3 grams-force (gf) may be set. In some embodiments, the strain percentage to be experienced by the LCM sample may be set.

Next a compression cycle (also referred to as loading cycle) may be performed by compressing the LCM sample via the probe at a displacement rate until a specific strain percentage is reached (block 708). In some embodiments, the LCM sample may be compressed at a displacement rate of 1 mm/second (mm/sec). The total energy stored at the end of the compression cycle may be recorded (block 710). The probe may be maintained in the loading cycle position for a compression time period (block 712). In some embodiments, the probe may be maintained in the loading cycle position for a compression time period of about 1 minute.

Next, a decompression cycle may be performed by withdrawing the probe at a displacement rate to allow the LCM sample to decompress (block 714). In some embodiments, the probe may be withdrawn at a displacement rate of about 1 mm/sec. The total energy released after the complete withdrawal of the probe may be recorded (block 716). As used herein, the term "complete withdrawal" refers to withdrawal of the probe such that the probe is no longer in contact with the LCM sample. In some embodiments, the probe may be withdrawn to at least the initial position of the probe before performance of the compression cycle. The coefficient of resilience of the LCM sample may be then be determined by dividing the desorbed strain energy released during the decompression cycle of the test by the absorbed strain energy stored by the sample during the compression cycle of the test (block 718). In some embodiments, steps of the process 700 may be performed multiple times to determine an average coefficient of resilience for an LCM. Additionally or alternatively, in some embodiments, multiple samples of LCM may be tested according to the process 700 to determine an average coefficient of resilience for an LCM. In some embodiments, samples of an LCM may be tested at different strain percentages to determine the coefficients of resilience of the LCM at the different strain percentages.

In some embodiments, the process 700 may be used to compare two or more LCMs and select one of the LCMs for use in a lost circulation zone in a well. For example, a sample of a first LCM may be resilience tested according to the process 700 to determine the coefficient of resilience, and a sample of a second LCM may be resilience tested according to the process 700 to determine a coefficient of resilience. The coefficient of resilience of the first LCM may be compared to the coefficient of resilience to determine which LCM has a resilience suitable for a particular lost circulation zone. For example, for vugular or cavernous lost circulation zones, an LCM having a greater coefficient of resilience or a coefficient of resilience above a specific threshold may be selected. The selected LCM may be introduced into a lost circulation zone in a wellbore, such as by adding the LCM to a drilling fluid and circulating the altered drilling fluid at a pump rate effective to position the altered drilling fluid into contact with the lost circulation zone. Advantageously, the portable resilience testing apparatus and techniques described in the disclosure provide a quantitative assessment of LCMs to enable selection of an LCM with optimal loss control capability for a specific loss circulation zone. The selection of an LCM with the optimal resilience may improve the lost control operations and reduce the loss of drilling fluids, thus reducing the overall cost and time of drilling and increasing efficiency.

Figure 8:
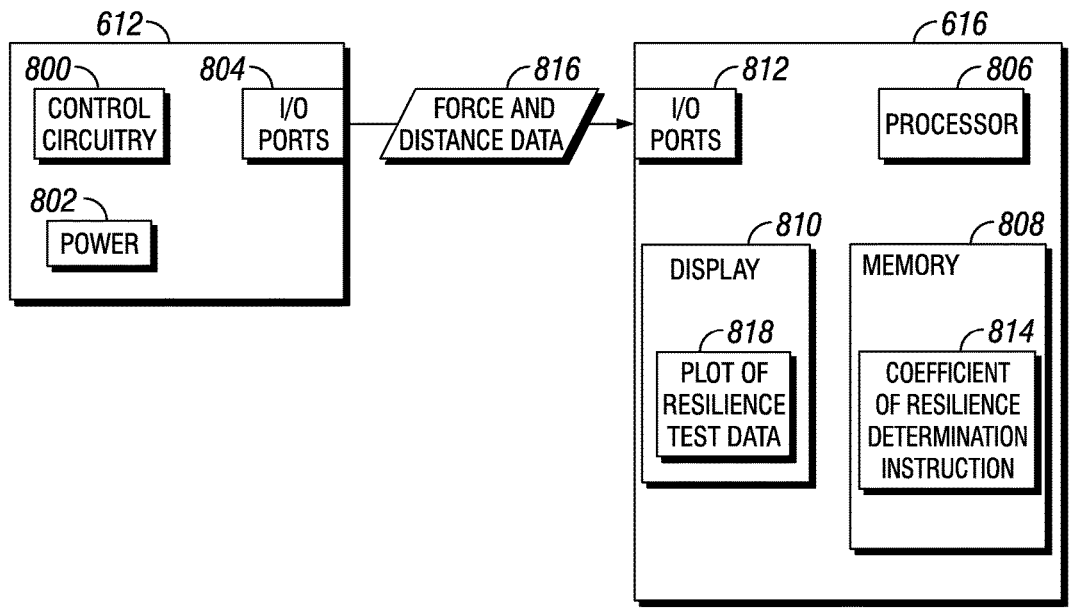
FIG. 8 is a block diagram of a base of a portable resilience testing apparatus and a computer apparatus in accordance with an embodiment of the disclosure.

FIG. 8 depicts a block diagram of the base 612 of the portable resilience testing apparatus 600 and the computer 616 apparatus in accordance with an embodiment of the disclosure. As noted above, the base 612 may form a housing that generally encloses some or all of the components of the base 612. In some embodiments, the base 612 may include control circuitry 800, a power source 802, and I/O ports 804. It should be appreciated that in other embodiments the base 612 may include other components provided for operation of the portable resilience testing apparatus 600. In some embodiments, the base 612 may include or form ergonomic features to enable portability and easier transport to a well site.

The control circuitry 800 may include logic to directly or indirectly control and monitor the parameters (for example, load, force, displacement, strain percentage, or any combination thereof) of a resilience test within preselected values. In some embodiments, the control circuitry 800 may be programmed with the parameters for a resilience test, such as using the computer 616 or, in some embodiments, hardware elements located on the base 612. For example, in some embodiments multiple strain percentages may be set to evaluate the coefficient of resilience under different loading and unloading conditions. The control circuitry 800 may transmit the parameters of a resilience test to the computer 616. In some embodiments, for example, the control circuitry 800 may include an application-specific integrated circuit (AISC) or a field-programmable gate array (FPGA).

In some embodiments, the base 612 may be formed from plastic, metal, or both. The base 612 may include one or more receptacles for receiving components of the portable resilience testing apparatus 600, such as a receptacle for the movement mechanism 608 and the connecting rod 609. The base 612 may include recesses or other features to house components, such as the I/O ports 804, that may provide for connection to external devices. In some embodiments, the base 612 may include or enclose active cooling components (for example, fans), passive cooling components (for example, heat sinks), for cooling components of the portable resilience testing apparatus 600.

The power source 802 may include power sources suitable for powering the components of the portable resilience testing apparatus 600. In some embodiments, the power source 802 may include one or more batteries. In some embodiments, power source 802 may include an AC to DC converter. In such embodiments, the portable resilience testing apparatus 600 may be connected to a source of AC (for example, an AC mains) via the I/O ports 804. In such embodiments, the power source 802 may provide DC to charge a battery, to power components of the portable resilience testing apparatus 600, or both.

The I/O ports 804 may enable the connection of external devices to the portable resilience testing apparatus 600. Embodiments of the portable resilience testing apparatus 600 may include any number and types of I/O ports 804, including universal serial bus (USB) ports, Firewire or IEEE-1394 ports, AC power connectors, and DC power connectors. Further, portable resilience testing apparatus 600 may use the input and output ports to connect to and send or receive data with other devices, such as the computer 616.

FIG. 8 also depicts a block diagram of the computer 616 connected to the base 612 of the portable resilience testing apparatus 600, such as via the I/O ports 804. As shown in FIG. 8, the computer 616 may include a processor 806, a memory 808, a display 812, and I/O ports 814. It should be appreciated that the computer 616 may include other components that are omitted for clarity. In some embodiments, the computer 616 may be a server, a desktop computer, a laptop computer, a tablet computer, a smartphone, or the like. For example, the computer 616 may a portable computer such as a laptop or tablet computer to accommodate the portability of the portable resilience testing apparatus 600 and transport to a well site.

The processor 806 (as used the disclosure, the term "processor" encompasses microprocessors) may include one or more processors having the capability to receive and process data, such as data received from the portable resilience testing apparatus 600 via the I/O ports 804 of the base 612. In some embodiments, the processor 806 may include an application-specific integrated circuit (AISC). In some embodiments, the processor 806 may include a reduced instruction set (RISC) processor. Additionally, the processor 806 may include a single-core processors and multicore processors and may include graphics processors. Multiple processors may be employed to provide for parallel or sequential execution of one or more of the techniques described in the disclosure. The processor 806 may receive instructions and data from a memory (for example, memory 808).

The memory 808 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 808 may be accessible by the processor 806. The memory 808 may store executable computer code. The executable computer code may include computer program instructions for implementing one or more techniques described in the disclosure. For example, the executable computer code may include coefficient of resilience of determination instructions 814 that determine a coefficient of resilience of an LCM using data received from the portable resilience testing apparatus. In some embodiments, the coefficient of resilience of determination instructions 814 may implement one or more elements of the process 800 described above and illustrated in FIG. 8. In some embodiments, the coefficient of resilience of determination instructions 814 may receive, as input, force and distance data 816. In some embodiments, the coefficient of resilience of determination instructions 814 may also display a plot of the force and distance data 816 received from the portable resilience testing apparatus 600. The plot 818 of the resilience test data may be stored in the memory 808 and, as shown in FIG. 8, may be displayed on the display 810.

The display 810 may include a cathode ray tube (CRT) display, liquid crystal display (LCD), an organic light emitting diode (OLED) display, or other suitable display. The display 606 may display a user interface (for example, a graphical user interface) that may display data received from the portable resilience testing apparatus 600. In accordance with some embodiments, the display 810 may be a touch screen and may include or be provided with touch sensitive elements through which a user may interact with the computer 616. In some embodiments, the display 810 may display resilience data plot 810 produced using the force and distance data in accordance with the techniques described herein. For example, an operator may view the resilience data plot 818 on the display 810 to evaluate an LCM for use in reducing or preventing lost circulation in a well.

The I/O ports 812 may enable the connection of external devices to the computer 616. Embodiments of the computer 616 may include any suitable number and type of I/O ports 812, including universal serial bus (USB) ports, Firewire or IEEE-1394 ports, AC power connectors, and DC power connectors. Further, the computer 616 may use the input and output ports to connect to and send or receive data with other devices, such as the base 612 of the portable resilience testing apparatus 600. For example, the I/O ports 812 may be connected to the I/O ports 804 via a cable or other connection device. The connection between the I/O ports 812 and the I/O ports 804 may enable the transfer of data from the portable resilience testing apparatus 600 to the computer 616.

In other embodiments, the base 612 and the computer 616 may each include network interfaces for wired or wireless network communication. In such embodiments, the base 612 may transfer data to the computer 616 over a wired or wireless network. For example, such networks, may include the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies.

EXAMPLES

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

The portable resilience testing apparatus 600 was testing using a test sample of coarse rubber particles having size in the range of greater than 1 mm to less than 4 mm. After placing the test sample in the test cell, resilience tests (that is, compression and decompression cycles) were conducted for strains of 20%, 30%, 40%, and 45% to generate various forces on the top of the test sample and simulate a range of overbalance pressures that would be experienced in a borehole environment. The results of the tests are shown in Table 1:

TABLE 1

RESULTS OF EXAMPLE TESTS USING TEST SAMPLE

| Sample | % Strain | Compressive Load (kgf) | Displacement at Selected Strain % (mm) | Area A (kgf · mm) | Area B (kgf · mm) | Coefficient of Resilience |
|---|---|---|---|---|---|---|
| A | 20% | 9.50 | 3.06 | 29.11 | 11.58 | 0.40 |
| B | 30% | 22.06 | 13.26 | 88.99 | 38.97 | 0.44 |
| C | 40% | 50.86 | 16.88 | 243.08 | 120.85 | 0.5 |

Example 1 (Sample A)

Figure 9:
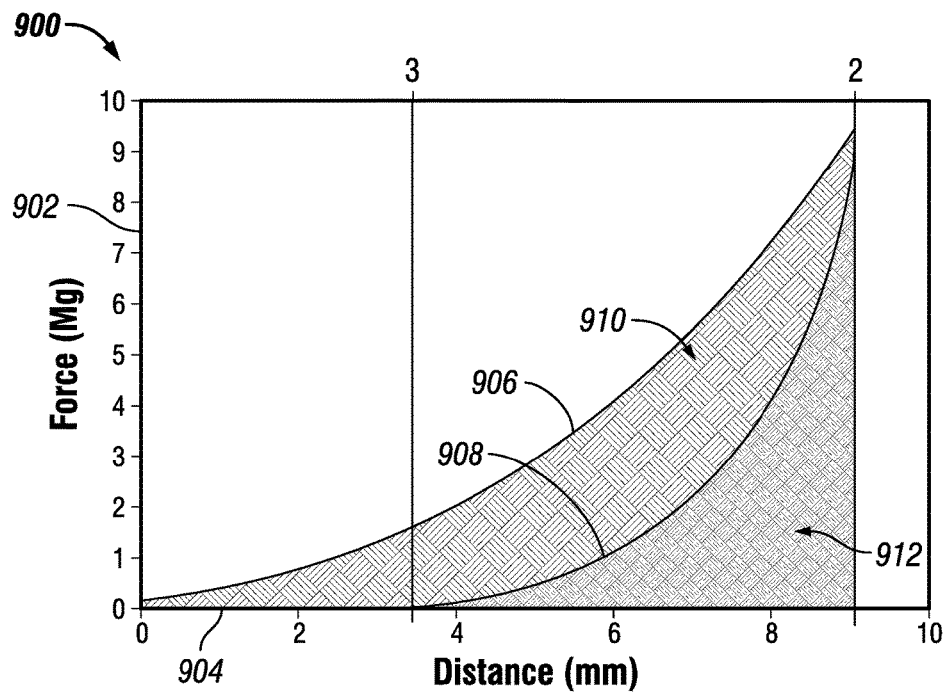
FIG. 9 is a plot of force vs. distance for a resilience test of an example Sample A in accordance with an embodiment of the disclosure.

Sample A was tested at a strain percentage of 20%. FIG. 9 depicts a plot 900 of force vs. displacement for the resilience test of Sample A illustrating the determination of the coefficient of resilience for the sample. As shown FIG. 9, the y-axis 902 depicts force and the x-axis 904 depicts distance moved by the probe. The line 906 in the plot 900 corresponds to the force-displacement curve generated during a compression cycle of the test of Sample A, and the line 908 corresponds to the force-displacement curve generated during a compression cycle of the test of Sample A. The shaded area 910 under the line 906 indicates the strain energy absorbed during the compression cycle of the test. The absorbed strain energy was calculated to be 29.11 kgf-mm. The shaded area 912 under the line 908 indicates the strain energy released during the decompression cycle of the test. The released strain energy was calculated to be 11.58 kgf-mm.

The coefficient of resilience for Sample A was calculated using Equation 1. Using the released strain energy of 11.58 kgf-mm and the absorbed strain energy of 29.11 kgf-mm, the coefficient of resilience of Sample A was about 0.40.

Example 2 (Sample B)

Figure 10:
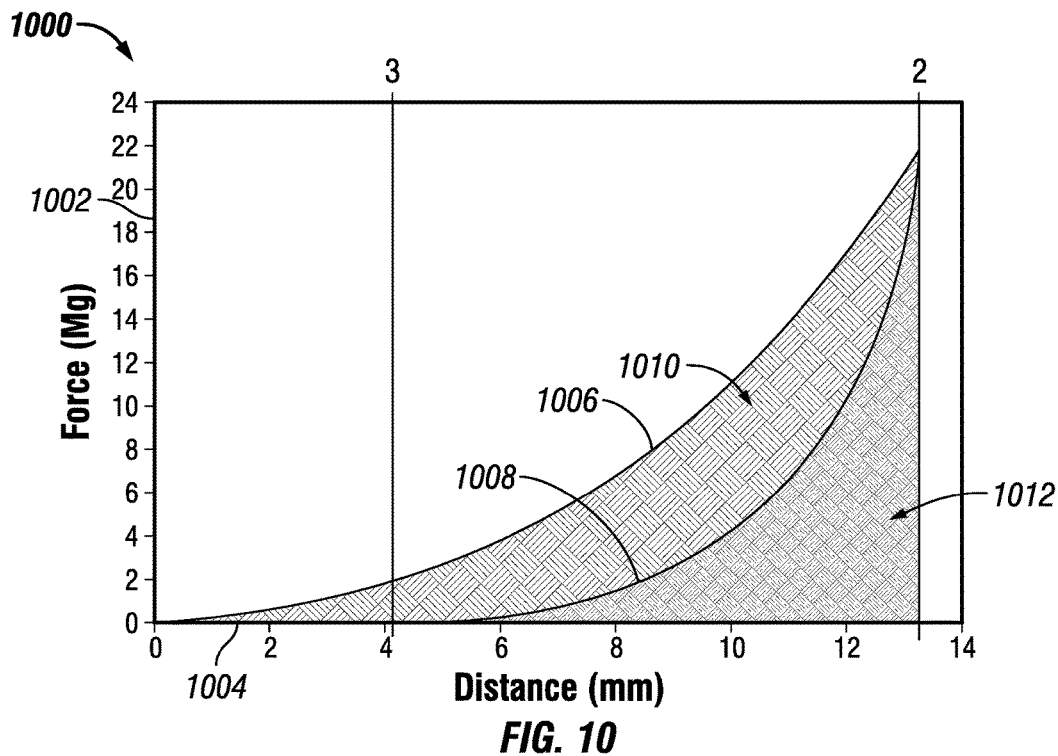
FIG. 10 is a plot of force vs. distance for a resilience test of an example Sample B in accordance with an embodiment of the disclosure.

Sample B was tested at a strain percentage of 30%. FIG. 10 depicts a plot 1000 of force vs. displacement for the resilience test of Sample B illustrating the determination of the coefficient of resilience for the sample. As shown FIG. 10, the y-axis 1002 depicts force and the x-axis 1004 depicts the distance moved by the probe. The line 1006 in the plot 1000 corresponds to the force-displacement curve generated during a compression cycle of the test of Sample B, and the line 1008 corresponds to the force-displacement curve generated during a compression cycle of the test of Sample B. As discussed above with regard to Sample A, the shaded area 1010 under the line 1006 indicates the strain energy absorbed during the compression cycle of the test, and the shaded area 1012 under the line 1008 indicates the strain energy released during the decompression cycle of the test. The absorbed strain energy corresponding to shaded area 1010 was calculated to be 88.99 kgf-mm, and the released strain energy corresponding to shaded area 1012 was calculated to be 38.97 kgf-mm.

The coefficient of resilience for Sample B was calculated using Equation 1. Using the released strain energy of 38.97 kgf-mm and the absorbed strain energy of 88.99 kgf-mm, the coefficient of resilience of Sample B was about 0.44.

Example 3 (Sample C)

Figure 11:
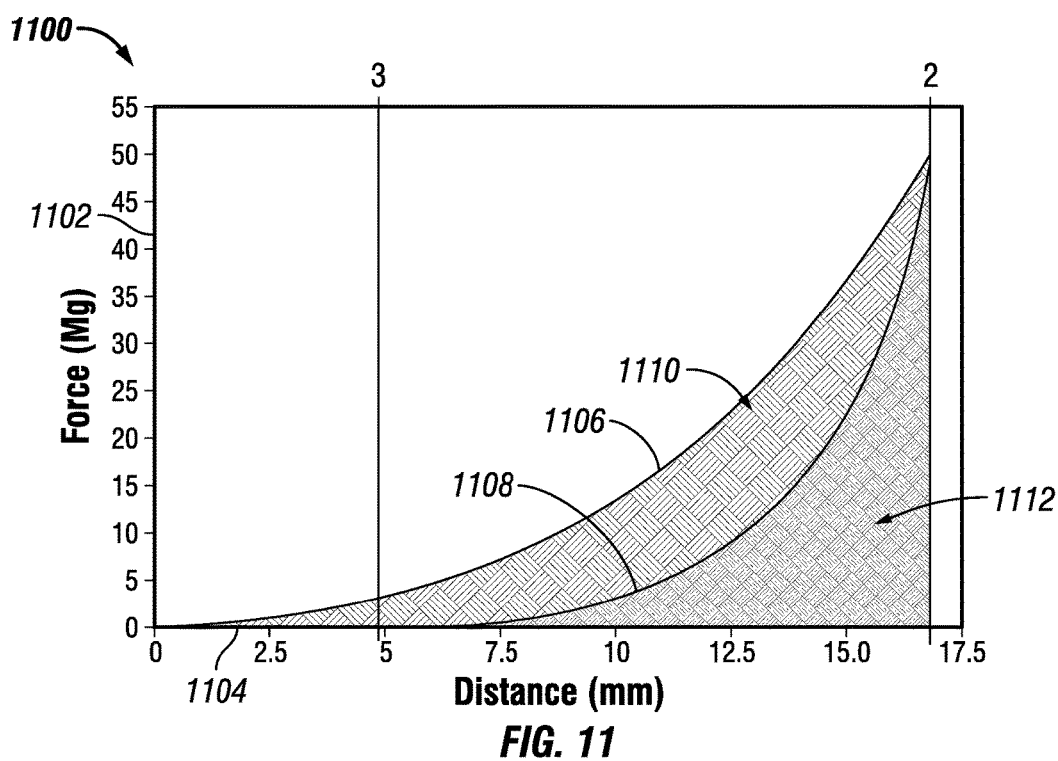
FIG. 11 is a plot of force vs. distance for a resilience test of an example Sample B in accordance with an embodiment of the disclosure.

Sample C was tested at a strain percentage of 40%. FIG. 11 depicts a plot 1100 of force vs. displacement for the resilience test of Sample C illustrating the determination of the coefficient of resilience for the sample. As shown FIG. 11, the y-axis 1102 depicts force and the x-axis 1104 depicts the distance moved by the probe. The line 1106 in the plot 1100 corresponds to the force-displacement curve generated during a compression cycle of the test of Sample C, and the line 1108 corresponds to the force-displacement curve generated during a compression cycle of the test of Sample C. As discussed above with regard to Samples A and B, the shaded area 1110 under the line 1106 indicates the strain energy absorbed during the compression cycle of the test, and the shaded area 1112 under the line 1108 indicates the strain energy released during the decompression cycle of the test. The absorbed strain energy corresponding to shaded area 1110 was calculated to be 243.08 kgf-mm, and the released strain energy corresponding to shaded area 1112 was calculated to be 120.85 kgf-mm.

The coefficient of resilience for Sample B was calculated using Equation 1. Using the released strain energy of 120.85 kgf-mm and the absorbed strain energy of 243.08 kgf-mm, the coefficient of resilience of Sample C was about 0.050.

The example tests described in the disclosure demonstrate the suitability of the portable resilience testing apparatus 600 and the resilience testing to determine the resilient behavior of LCMs and show the capability of the portable resilience testing apparatus 600 to determine a coefficient of resilience at different strain percentages Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. An apparatus for determining the coefficient of resilience of a lost circulation material (LCM), comprising:
   a test cell having an interior chamber configured to contain a sample of the LCM, the test cell having an open end and closed end defining the interior chamber;
   a probe configured to insert into the open end of the test cell, the probe comprising a disc-shaped probe foot and a probe leg;
   an arm coupled to the probe and configured to apply a load to the probe such that a force is applied to the LCM sample via movement of the probe over a first displacement during a compression cycle, the arm further configured to release the load applied to the probe such that the force is removed via movement of the probe over a second displacement during a decompression cycle;
   a processor;
   a non-transitory computer-readable memory accessible by the processor, the memory having executable code stored thereon, the executable code comprising a set of instructions that causes the processor to perform operations comprising:
   determining a strain energy absorbed by the LCM sample during the compression cycle using the first displacement;
   determining a strain energy released by the LCM sample during a decompression cycle using the second displacement; and
   determining a coefficient of resilience by dividing the released strain energy by the absorbed strain energy.

2. The apparatus of claim 1, wherein the operations comprising providing a plot of force versus distance based on the force applied to the LCM sample and the distance between the first position and the second position on a display accessible by the processor.

3. The apparatus of claim 1, comprising a base, wherein the test cell is coupled to the base.

4. The apparatus of claim 1, wherein the arm is coupled to the base via a movement mechanism.

5. The apparatus of claim 1, wherein the base comprises a port, wherein the port is configured to connect to the processor via a wired connection.

6. The apparatus of claim 1, wherein the probe arm and probe leg comprise aluminum.

7. The apparatus of claim 1, wherein the movement of the probe over the first displacement occurs between a first position and a second position, and the movement of the probe over the second displacement occurs between the second position and the third position.

8. The apparatus of claim 7, wherein the first position and the third position are the same.

9. The apparatus of claim 7, wherein the arm is further configured to maintain the probe in the second position for a time period before movement of the probe to the third position.

10. A method for determining the coefficient of resilience of a lost circulation material (LCM), the method comprising:
   applying a force to LCM a sample of the LCM contained in a test cell via movement of a probe inserted into an open end of a test cell from a first position to a second position during a compression cycle, the first position and second position defining a first displacement;
   determining a strain energy absorbed by the LCM sample using the first displacement;
   releasing the force applied to the LCM sample via displacement of the probe from the second position to a third position during a decompression cycle, the second position and third position defining a second displacement;
   defining a strain energy released using the second displacement; and
   determining a coefficient of resilience by dividing the released strain energy by the absorbed strain energy.

11. The method of claim 10, wherein the force is at least 3 grams-force (gf).

12. The method of claim 10, wherein the movement of the probe occurs over a displacement rate.

13. The method of claim 12, wherein the displacement rate is at least 1 millimeter/second (mm/sec).

14. The method of claim 10, comprising maintaining the probe in the second position for a time period.

15. The method of claim 14, wherein the time period is at least one minute.

16. The method of claim 10, wherein the first position and the third position are the same.

17. An apparatus for determining the coefficient of resilience of a lost circulation material (LCM), comprising:
   a base comprising a control circuit and a power source;
   a test cell coupled to the base and having an interior chamber configured to contain a sample of the LCM, the test cell having an open end and closed end defining the interior chamber;
   a probe configured to move within the interior chamber of the test cell;
   a connecting rod coupled to the base;
   an arm coupled to the probe, the arm configured to apply a load to the probe in response such that a force is applied to the LCM sample via movement of the probe over from a first position to a second position during a compression cycle, the arm further configured to release the load applied to the probe such that the force is removed via movement of the probe from the second position to a third position during a decompression cycle, the first position and the second position defining a first displacement of the probe and the second position and the third position defining a second displacement of the probe.

18. The apparatus of claim 17, wherein the arm is further configured to maintain the probe in the second position for a time period before movement of the probe to the third position.

19. The apparatus of claim 17, wherein the first position and the third position are the same.

20. The apparatus of claim 17, comprising:
   a first position limiter coupled to the connecting rod; and
   a second position limiter coupled to the connecting rod, wherein the first position limiter is configured to define the second position of the probe and the second position limiter is configured to engage the arm to define the third position of the probe.

* * * * *